United States Patent
Madjarac

[11] Patent Number: 5,881,916
[45] Date of Patent: Mar. 16, 1999

[54] TUBE UNCLOGGING DEVICE

[76] Inventor: Michael G. Madjarac, 42320 Edward Cir., Columbiana, Columbiana County, Ohio 44408

[21] Appl. No.: 800,666

[22] Filed: Feb. 14, 1997

[51] Int. Cl.⁶ .................................................. A61B 17/00
[52] U.S. Cl. ................................ 222/102; 251/6; 606/209
[58] Field of Search ..................................... 222/102, 101; 251/6, 10, 9; 606/209; 417/476

[56] References Cited

U.S. PATENT DOCUMENTS

| | | | |
|---|---|---|---|
| 1,983,462 | 12/1934 | Johnson | 222/102 |
| 3,194,452 | 7/1965 | Sanderford . | |
| 3,648,701 | 3/1972 | Botts . | |
| 3,847,370 | 11/1974 | Engelsher . | |
| 4,164,223 | 8/1979 | Munib . | |
| 4,266,751 | 5/1981 | Akhavi | 222/102 |
| 4,452,244 | 6/1984 | Chin | 606/209 |
| 4,517,702 | 5/1985 | Jackson . | |
| 4,585,440 | 4/1986 | Tchervenkov et al. . | |
| 4,615,472 | 10/1986 | Nash . | |
| 5,030,213 | 7/1991 | Rumberger et al. . | |
| 5,141,503 | 8/1992 | Sewell, Jr. . | |
| 5,295,278 | 3/1994 | Condon et al. . | |

Primary Examiner—Steven O. Douglas
Attorney, Agent, or Firm—Frederic E. Naragon

[57] ABSTRACT

An instrument for use with resilient tubing such as wound drainage tubing, catheters, chest tubing, common duct T tubing, I.V. tubing and other deformable tubing comprising in combination a U-shaped body having a pair of cylindrical rollers mounted for rotation on each end of the opened end of the U-shaped body, said rollers being oriented parallel to each other and to the sides of the U-shaped body, spaced apart and in relationship for movement into and out of engagement with opposite sides of the tubing whereby the user's hand can grasp the U-shaped body for moving the rollers at right angles to and against the tubing while also moving the rollers along the length of the tubing and where the U-shaped body has sufficient spring force to retain the device on the tubing when not in use and where the rollers are secured by a pair of slotted tabs affixed to each side of the open end of the U-shaped body and allow the rollers to be removed and inter-changed with rollers of various sizes to accommodate correspondingly sized tubing and the rollers and tabs are kept in allignment by an end retainer and a guide retainer disposed at the ends of the cylindrical rollers, respectively.

2 Claims, 2 Drawing Sheets

TUBE UNCLOGGING DEVICE

BACKGROUND OF THE INVENTION AND SUMMARY OF THE INVENTION

The present invention relates generally to a tube unclogging device such as for clearing and dislodging the contents of wound drainage tubes, catheters, chest tubing, common duct T tubing, I.V. tubing and other deformable tubing. The device includes generally a U-shaped body having a pair of rollers disposed at the opened end of the U-shaped body and a drainage tube is placed between the rollers and the spring force of the body retains the device on the tube. The rollers are periodically squeezed together by the operator and rolled along the drainage tube to keep the tube clear and unclogged. The rollers may be removed from the device and replaced with rollers of other sizes according to the size of the tubing.

The invention provides exceptional advantages when employed particularly in the medical field in that the present invention is simple and inexpensive in construction, can be fabricated from synthetic plastic materials, and can be made disposable. In addition, the present invention may be used by the patient without the assistance of another party in unclogging a tube inserted into the patient, particularly following surgery. In addition, the present invention may be left in tact on the tubing when not in use and readily available in the event of sudden clogging or other emergency situations.

The present invention comprises a U-shaped body so that the user's hand can easily grasp the device and compress the tubing with the rollers disposed at the opened end of the device while simultaneously moving the instrument along the tubing creating a squeeze effect for moving or propelling contents within the tubing along the tubing.

A further advantage of the present invention is the interchangability of the rollers in the device to correspond with the size of tubing required to be cleaned. The user of the present device may insert rollers of varying sizes corresponding to tubing of like size and thus it is unnecessary to have a separate device for each size of tubing in use.

Heretofore, the prior art has disclosed patents for the cleaning of tubing through use of plungers, brushes, and other items but the prior art does not disclose any patents teaching of the unique characteristics of the present invention. Some of the patents of the prior art are listed as follows:

| | | |
|---|---|---|
| U.S. Pat. No. 5,295,278 | Condon et al. | March 22, 1994 |
| U.S. Pat. No. 5,141,503 | Sewell, Jr. | Aug. 25, 1992 |
| U.S. Pat. No. 5,030,213 | Rumberger et al. | July 9, 1991 |
| U.S. Pat. No. 4,615,472 | Nash | Oct. 7, 1986 |
| U.S. Pat. No. 4,585,440 | Tchervenkov et al. | April 29, 1986 |
| U.S. Pat. No. 4,517,702 | Jackson | May 21, 1995 |
| U.S. Pat. No. 4,164,223 | Munib | Aug. 14, 1979 |
| U.S. Pat. No. 3,847,370 | Engelsher | Nov. 12, 1974 |
| U.S. Pat. No. 3,648,701 | Botts | March 14, 1972 |
| U.S. Pat. No. 3,194,452 | Sanderford | July 13, 1965 |

U.S. Pat. No. 5,295,278 issued to Duane R. Condon on Mar. 22, 1994, pertains to a cleaning tool for preparing the surfaces of pipes and fittings for soldering and other functions. The invention teaches of a generally U-shaped hand-held device but does not provide for rollers for compressing the tubing or pipe and does not provide for a means for positively retaining the device on the tubing or pipe when not in use as is provided in the present invention. In addition, the invention of Condon is primarily for pipes and the cleaning of the exterior surface of pipes not related to the medical field.

U.S. Pat. No. 5,141,503 issued to Frank K. Sewell, Jr. on Aug. 25, 1992, pertains to a wound drainage system having a wound drainage catheter with an apertured distal end and a closed reservoir system. The invention provides for a plug and thread for pulling the plug through the tubing or lumen to clear the catheter of occluded material. The invention pertains to a device for internally cleaning the tubing. The present invention is distinguishable and provides for an exterior cleaning device to be hand-held by the user and for compressing of the tubing exteriorly and does not require the use of a suction device, reservoir or otherwise.

U.S. Pat. No. 5,030,213 issued to William R. Rumberger et al. on Jul. 9, 1991, pertains to a catheter router assembly for clearing salt blockages in a catheter which has been previously inserted into a person. The device discloses a cable with a cutter which is routed through the interior portion of the tubing to clear the tubing of debris. The present invention is distinguishable in that the present invention provides for a device used for the exterior of the tubing which compresses the tubing and squeezes the tubing to move any clog or debris along the interior of the tubing to the designated area of disposal.

U.S. Pat. No. 4,615,472 issued to John Nash on Oct. 7, 1986, pertains to a device for the placement or location of catheters internally within a patient and provides for a device which exteriorly urges the tubing longitudinally into a patient for the appropriate location. The invention does not teach of any cleaning device for cleaning or clearing the tubing as is provided in the present invention.

U.S. Pat. No. 4,585,440 issued to Jean Tchervenkov et al. on Apr. 29, 1986, relates to an invention for clearing a catheter tube by a plunger means internal to the tubing when the catheter is not in use. The present invention teaches of an external method of cleaning or clearing tubing by a hand-held instrument not requiring the use of a plunger internal to the tubing.

U.S. Pat. No. 4,517,702 issued to Frank W. Jackson on May 21, 1985, teaches of a self-contained cleaning device for endoscopic instruments of the type inserted into a human or animal body which does not provide for the cleaning of the interior portion of the tubing but only provides for the scrubbing of the exterior of the tubing through a sponge body for the removal of undesirable materials and for the sterilization of the tubing for a later use. The patent issued to Jackson, while providing for a slight squeezing of the external portion of the tubing does not provide rollers for squeezing and moving of any substance within the tubing and does not provide for the interchangeability of rollers to accommodate tubings of various sizes as is provided in the present invention.

U.S. Pat. No. 4,164,223 issued to Hamza I. Munib on Aug. 14, 1979, while providing for a pair of rollers mounted on shafts which are hinged together at one end and a handle for grasping by the user and for moving the rollers along the exterior of tubing, the invention however does not provide for means for positively retaining the device on the tube when not in use and does not provide for the interchangeability of rollers to accommodate various sizes of tubing as is provided in the present invention. In addition, the patent to Munib is of complicated construction and expensive to manufacture and is not readily manufactured for disposable use as is provided in the present invention.

U.S. Pat. No. 3,847,370 issued to Harvey J. Engelsher on Nov. 12, 1974, provides for a tube servicing device having a pair of rollers pushed together to pinch a tube between them which expels materials within the tube as the frame of the device is drawn along the tube, however, the device requires threading onto the tubing rather than being able to access the tube at any point along its length as is provided in the present invention.

U.S. Pat. No. 3,648,701 issued to Marion Botts on Mar. 14, 1972, pertains to a forceplike instrument having rollers for clearing the contents of flexible tubing. The invention requires the threading of the tubing through a retaining link and requires the operator to squeeze the scissorlike grip of the device and manipulate the device along the tubing. The invention does not provide for the interchangeability of rollers to accommodate tubing of different sizes nor does it provide for any means of retaining the device on the tube when not in use as is provided in the present invention. In addition, the patent to Botts is of complicated construction and is expensive to manufacture and not readily disposable after use as is provided in the present invention.

U.S. Pat. No. 3,194,452 issued to E.C. Sanderford on Jul. 13, 1965, relates to a tube stripper and comprises a hand-held instrument pivotally connected at one end with rollers adapted at the other end to squeeze tubing between the rollers to clean the interior portion of the tubing. The device of Sanderford does not provide for the interchangeability of rollers to accommodate tubing of various sizes and does not provide for any means for positively retaining the device on the tube when not in use as is provided in the present invention.

BRIEF DESCRIPTION OF THE DRAWINGS

For a better understanding of the invention reference should be made to the accompanying drawings wherein.

Figure 1:
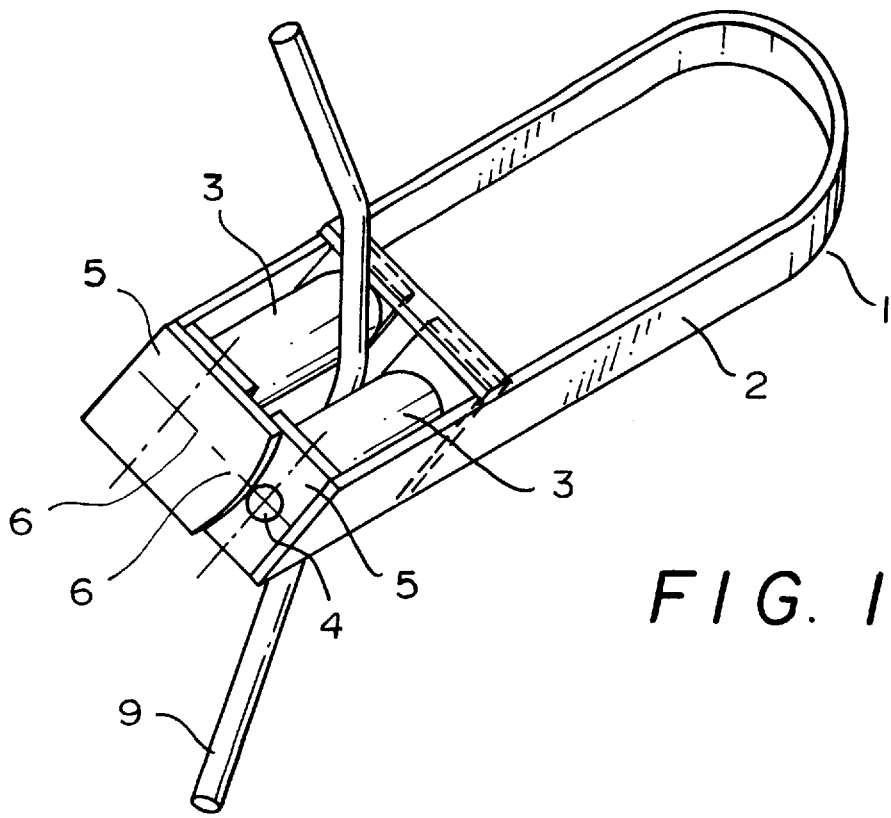
FIG. 1 is a perspective view of the preferred embodiment of the present invention with tubing in position.

LISTING OF ELEMENTS 1 is the present invention;
2 is the u-shaped body;
3 is a cylindrical roller;
4 is a roller end;
5 is a tab;
6 is a slot;
7 is an end retainer;
8 is a guide retainer;
9 is tubing.

DETAILED DESCRIPTION OF THE DRAWINGS

Reference is now made to the drawings wherein the present invention is illustrated in detail and wherein similar components bear the same reference numeral throughout the several views.

FIG. 1 is a perspective view of the preferred embodiment of the present invention 1 with tubing 9 in position and illustrates the U-shaped body 2, rollers 3, roller end 4, tabs 5, and slots 6.

Figure 2:
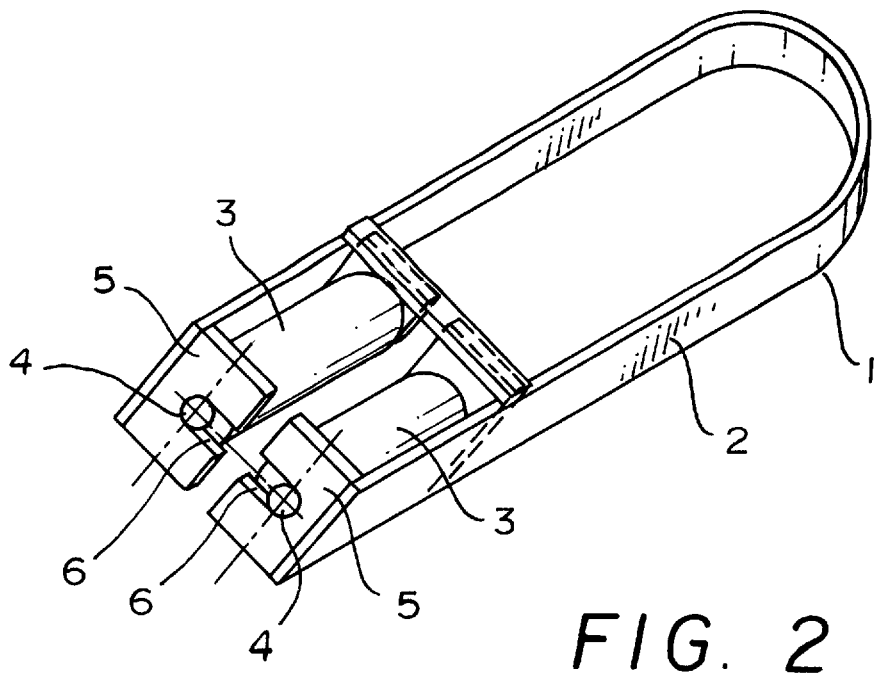
FIG. 2 is a perspective view of the preferred embodiment of the present invention.

FIG. 2 is a perspective view of the preferred embodiment of the present invention 1 and illustrates U-shaped body 2, rollers 3, roller ends 4, tabs 5, and slots 6.

Figure 3:
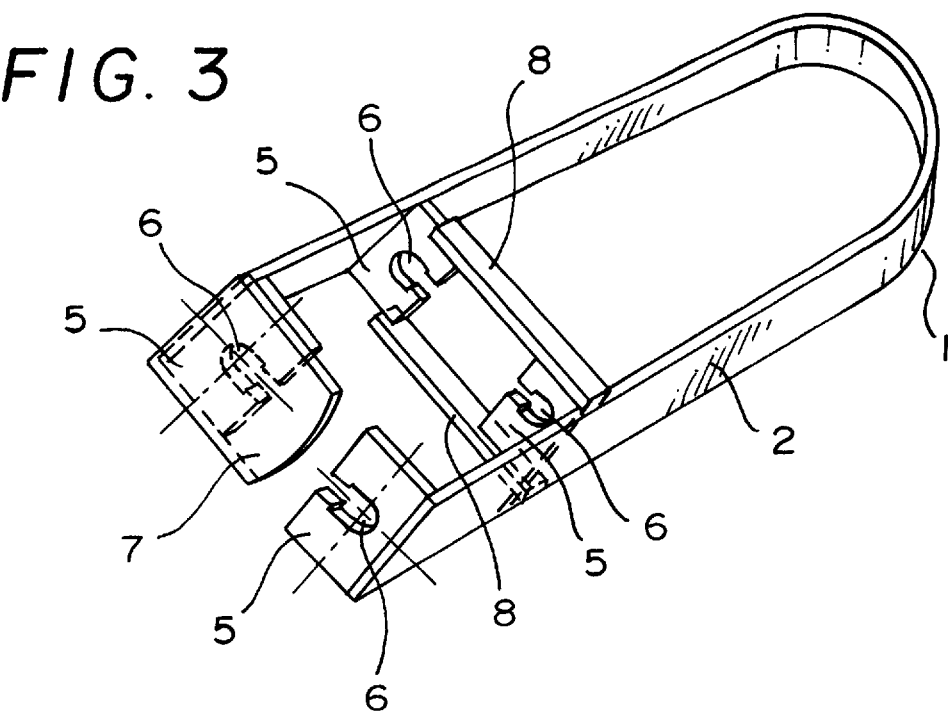
FIG. 3 is a perspective view of the preferred embodiment of the invention with rollers removed.

FIG. 3 is a perspective view of the present invention 1 with cylindrical rollers 3 removed and illustrates the U-shaped body 2, tabs 5, slots 6, retainer end 7, and guide retainer 8.

Figure 4:
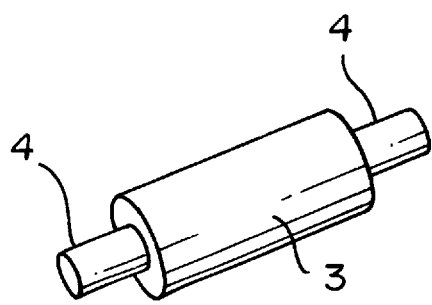
FIG. 4 is a perspective view of a roller and roller end.

FIG. 4 is a perspective view of a cylindrical roller 3 and further illustrates roller ends 4.

Figure 5:
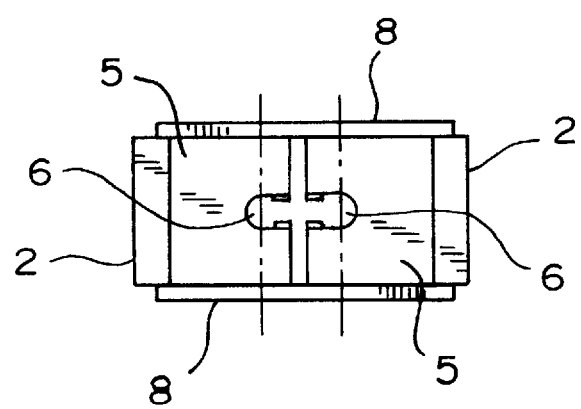
FIG. 5 is an end view of the present invention with cylindrical rollers removed.

FIG. 5 is an end view of the present invention 1 with cylindrical rollers 3 removed and illustrates U-shaped body 2, tabs 5, slots 6 and guide retainer 8.

DESCRIPTION OF THE PREFERRED EMBODIMENT

Referring to FIGS. 1 through 5 the preferred embodiment of the present invention is a device for use in unclogging wound drainage tubes, catheters, chest tubing, common duct T tubing, I.V. tubing, and other deformable tubing and comprises a U-shaped body having a pair of rollers removably and interchangeably disposed at on the opened end of the U-shaped body wherein a 10 drainage tube is placed between the rollers and a spring force of the body of the device retains the device on the tube. The operator in use squeezes the body which compresses the rollers against the tubing and rolls the device along the distance of the tube to keep the tube clear and unclogged. The rollers may be removed from the U-shaped body and replaced with rollers of other sizes according to the size of the tubing. In addition, the device is disposable and is of simple construction and inexpensive to manufacture. When not in use, the spring effect of the body of the device allows the device to be retained on the tube and the device may be inserted on the tube at any desired location. The rollers are cylindrical shaped with smaller diameter roller ends of cylindrical shape disposed at each end of each cylinder and one roller is removably secured to each side of the open end of the U-shaped body by a pair of slotted tabs affixed to each side of the open end of the U-shaped body and inwardly and perpendicular to the surface of the body and the slots are adapted to accept the roller ends of the cylindrical rollers to secure the rollers in place and to allow the rollers to turn within the slots. An end retainer is disposed perpendicular and inwardly on one side at one end of the open end of the U-shaped body and overlaps two of the slotted tabs affixed at each side of the end of the open end of the U-shaped body and keeps the rollers and slotted tabs in alignment.

A guide retainer is disposed inwardly and perpendicular to the U-shaped body on one side of the open end of the U-shaped body and keeps the other two of the slotted tabs affixed on each side of the open end of the U-shaped body and rollers in alignment.

The device ideally may be constructed of synthetic plastic material and is thus light-weight, of low cost and disposable.

Although the invention has been described in preferred form with a certain degree of particularity, it is understood that the present disclosure of the preferred form has been made only by way of example and numerous changes in the details of construction and the combination arrangement of parts may be resorted to without departing from the spirit and scope of the invention as herein after claimed.

What is claimed is:

1. An instrument for use with resilient tubing comprising in combination a U-shaped body having a solid arcuate closed end, two sides that extend in a longitudinal direction from said arcuate closed end and terminate in an open end, a pair of cylindrical rollers disposed for rotation on each end of the open end of the U-shaped body, said rollers being oriented parallel to each other and to the longitudial direction of the sides of the U-shaped body, spaced apart, and in relationship for movement into and out of engagement with opposite sides of the tubing whereby the user's hand can grasp the U-shaped body for moving the rollers at right angles to and against the tubing while also moving the rollers along the length of the tubing and where the U-shaped body has sufficient spring force to retain the device on the tubing when not in use and where the rollers are mounted by means allowing the rollers to turn and to be removed and interchanged with rollers of various sizes to accommodate correspondingly sized tubing.

2. An instrument for use with resilient tubing comprising in combination a U-shaped body having sides, a pair of cylindrical rollers disposed for rotation on each end of an open end of the U-shaped body, said rollers being oriented parallel to each other and to the sides of the U-shaped body, spaced apart, and in relationship for movement into and out of engagement with opposite sides of the tubing whereby the user's hand can grasp the U-shaped body for moving the rollers at right angles to and against the tubing while also moving the rollers along the length of the tubing and where the U-shaped body has sufficient spring force to retain the device on the tubing when not in use and where the rollers are mounted by means allowing the rollers to turn and to be removed and interchanged with rollers of various sizes to accommodate correspondingly sized tubing, wherein the rollers are cylindrical in shape and are of a designated diameter and wherein roller ends of each roller are of a smaller designated diameter and of cylindrical shape and wherein the means for securing the rollers to the U-shaped body comprises two pair of tabs with one pair disposed inwardly and perpendicular to each end of the U-shaped body and contain slots slightly smaller in size than the roller ends and secure one roller between each pair of tabs by a pinching effect and wherein the rollers and two of the four tabs disposed on each side of the open end of the U-shaped device are kept in alignment by a retainer end disposed perpendicular and inwardly on one side at the open end of the U-shaped body and overlaps the two tabs disposed at the end of each side of the U-shaped body, and wherein a guide retainer is disposed perpendicular and inwardly to the U-shaped body side on one side of the U-shaped body and keeps alignment of the rollers and other two tabs disposed on each side of the open end of the U-shaped body.

\* \* \* \* \*